United States Patent
Aporta et al.

(10) Patent No.: US 9,867,726 B2
(45) Date of Patent: Jan. 16, 2018

(54) DEVICE FOR INSERTING AN IMPLANT

(75) Inventors: Carsten Aporta, Bochum (DE); Jörg Ascherfeld, Hattingen (DE); Ralf Hannes, Dortmund (DE); Hermann Monstadt, Bochum (DE)

(73) Assignee: Phenox GmbH, Bochum (DE)

( * ) Notice: Subject to any disclaimer, the term of this patent is extended or adjusted under 35 U.S.C. 154(b) by 673 days.

(21) Appl. No.: 13/700,376

(22) PCT Filed: May 25, 2011

(86) PCT No.: PCT/EP2011/002592
§ 371 (c)(1),
(2), (4) Date: Feb. 11, 2013

(87) PCT Pub. No.: WO2011/147567
PCT Pub. Date: Dec. 1, 2011

(65) Prior Publication Data
US 2013/0138198 A1    May 30, 2013

(30) Foreign Application Priority Data
May 28, 2010    (DE) .......................... 10 2010 021 947

(51) Int. Cl.
*A61F 2/95*    (2013.01)
*A61B 17/12*    (2006.01)

(52) U.S. Cl.
CPC ............ *A61F 2/95* (2013.01); *A61B 17/1214* (2013.01); *A61B 17/12113* (2013.01); *A61B 17/12022* (2013.01); *A61B 2017/12063* (2013.01); *A61B 2017/12072* (2013.01); *A61B 2017/12086* (2013.01); *A61F 2002/9505* (2013.01)

(58) Field of Classification Search
CPC .... A61B 2017/12063; A61B 17/12022; A61B 2017/1205; A61B 2017/12054; A61B 17/12109; A61B 17/12113
See application file for complete search history.

(56) References Cited

U.S. PATENT DOCUMENTS

| | | | |
|---|---|---|---|
| 7,524,322 B2 * | 4/2009 | Monstdt et al. | 606/200 |
| 2006/0282112 A1 * | 12/2006 | Griffin | 606/200 |
| 2007/0270942 A1 * | 11/2007 | Thomas | 623/1.46 |

OTHER PUBLICATIONS

Pound, Bruce G., "Electrochemical behavior of cobalt-chromium alloys in a simulated physiological solution", Journal of Biomedical Materials Research Part A, Bd. 94A, Nr. 1, Feb. 2, 2010, pp. 93-102.

* cited by examiner

*Primary Examiner* — Diane Yabut
(74) *Attorney, Agent, or Firm* — Berliner & Associates

(57) ABSTRACT

The invention relates to a device having an endovascular implant (1) for the introduction into blood vessels or body cavities of the human or animal body and an insertion aid (2), wherein the implant (1) and the insertion aid (2) being connected to each other via a detachment element (3) designed to be electrolytically corrodible so that after the implant (1) has been inserted into the body and a voltage has been applied an at least partial dissolution of the detachment element (3) takes place causing the implant (1) to be separated from its the insertion aid (3), with the detachment element (3) being made of a cobalt-chrome alloy containing at least 20% w/w cobalt and 10 to 40% w/w chrome.

19 Claims, 1 Drawing Sheet

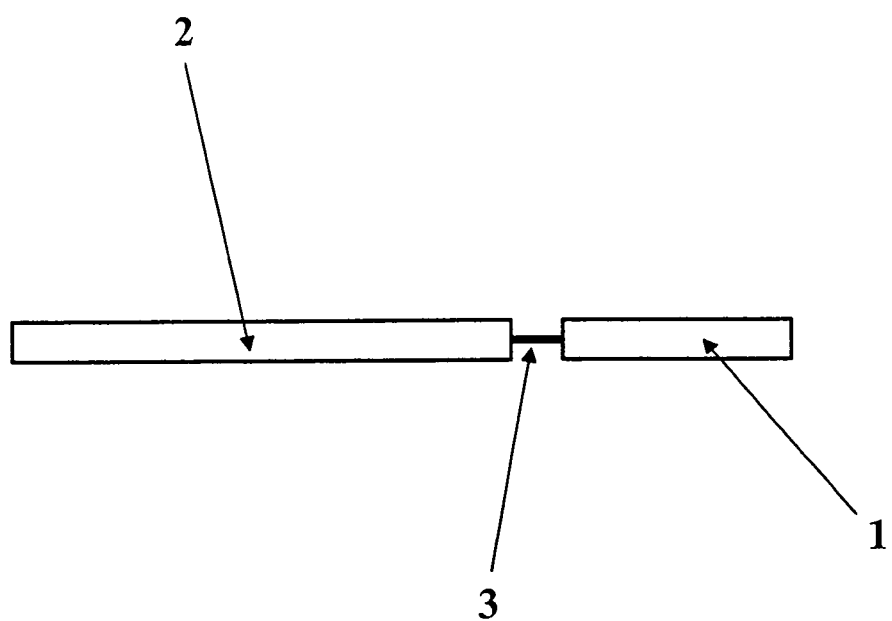

DEVICE FOR INSERTING AN IMPLANT

The invention relates to a device comprising an endovascular implant which is to be introduced into blood vessels or body cavities of the human or animal body and an insertion aid, wherein the implant and the insertion aid being connected to each other via a detachment element designed so as to be eiectrolytically corrodible in such a manner that after the implant has been introduced into the body said detachment element is at least partially dissolved by applying a voltage resulting in the implant being separated from the insertion aid.

The use of endovascular techniques for the occlusion of body cavities or vessels such as arteries, veins, fallopian tubes or vascular deformities (for example, vascular aneurysms) is known in the art. For this purpose, so-called occlusion is helixes, for example, are introduced by means of an endovascular guide wire serving as insertion aid through a catheter into the cavity to be occluded and deposited therein. Also known is the placement of other implants, for example stents.

To detach the implant from the insertion aid various methods are known from prior art. Aside from mechanical methods the electrolytic severance of stainless steel wire ends as initially described for electro-coagulation by Thompson et al, as well as McAlister et al. in 1979 has in particular proved its worth in this context (Radiology 133: 335-340, November 1979; AJR 132:998-1000, June 1979). Based on this, also publication EP 0 484 468 B1 has proposed a device for the implantation of occlusion helixes involving an electrolytic detachment method.

Irrespective of the type of the implant to be inserted at a given time the attending physician always endeavors to keep the detachment time as short as possible to make sure an implant displacement or other undesirable events cannot occur during detachment. For this reason various materials were used in the past for the detachment element arranged between the implant and the insertion aid with a view to enabling said element to be quickly dissolved as soon as a voltage is applied. For example WO 03/017852 A1 has proposed using a stainless steel material which was first subjected to a pre-corrosion process involving a heat treatment.

It is therefore the objective of the present invention to propose means based on a device of the kind first mentioned above that are suited to further bring down the time span required to detach the implant from the insertion aid.

As proposed by the invention this objective is reached by providing a device comprising an endovascular implant for the introduction into blood vessels or is body cavities of the human or animal body and an insertion aid, wherein the implant and the insertion aid being connected to each other via a detachment element designed to be electrolytically corrodible so that after the implant has been inserted into the body and a voltage has been applied an at least partial dissolution of the detachment element takes place causing the implant to be separated from the insertion aid, with the detachment element being made of a cobalt-chrome alloy containing at least 20% w/w cobalt and 10 to 40% w/w chrome.

Surprisingly, it has been found that detachment elements based on cobalt-chrome alloys enable extremely short detachment times to be attained after a voltage has been applied. As a rule, these are below 30 s (2 V, 2 mA). Detachment times of merely 5 s can be achieved as well, said periods depending of course also on the thickness of the detachment element. This is to be considered a significant improvement compared with the prior art time spans of between 20 and 40 s based on otherwise identical conditions as for instance stated in WO 2005/070308 A2.

Suitable cobalt-chrome alloys are those distributed by the company of Deloro under the tradename of Stellite®. These are cobalt-chrome alloys that may contain proportions of tungsten, nickel, molybdenum, iron and other elements. Stellites® are highly wear resistant materials which are in particular employed for components exposed to high load conditions. For that reason, it was even more surprising to find that detachment elements made of Stellite® could be very quickly dissolved electrolytically.

Preferably, the maximum cobalt content is 70% w/w and, in particular, contents ranging between 30 and 60% w/w are considered advantageous. The chrome content may in particular amount to between 15 and 30% w/w.

Additional elements may improve the characteristics of the detachment element. An alloy containing between 4 and 12% w/w of molybdenum and/or between 5 and 20% w/w of tungsten offers advantages in this respect.

If considered necessary, the nickel, manganese or iron contents may be significantly higher and in the case of manganese and iron may amount to 30% w/w maximum. The nickel content may range between 8 and 40% w/w.

Examples of useful cobalt-chrome alloys are those distributed under the tradename of Elgiloy® or Phynox®. The German material number is 2.4711. The alloy contains 40% w/w of cobalt, 20% w/w of chrome, 16% w/w of iron, 15% w/w of nickel and 7% w/w of molybdenum and, if thought expedient, minor amounts of manganese, carbon, silicon, phosphorus, sulfur and beryllium.

Another usable alloy is Stellite®25 which contains, among other constituents, approx. 50% w/w of cobalt, 20% w/w of chrome, 10% w/w of nickel and 15% w/w of tungsten. Stellite®21 is another example, said alloy containing approx. 63% w/w of cobalt, 28% w/w of chrome and 6% w/w of molybdenum.

The insertion aid is preferably a customary guide wire of proven design for the purpose of passing occlusion helixes or stents through a catheter to the relevant placement site. The insertion aid is connected to the proximal end of the implant, i.e. in the direction from where the physician pushes the implant forward.

The implant may be an occlusion helix or a stent. The implant may as well be a stent-like system devised so as to influence the flow of blood, said implant may either be of braided design, be laser-cutout of a metal or plastic sheet or fabricated with the aid of suitable plastic membranes. Basically however, the invention can be used for any kind of endovascular implant which is to be transferred to its destination by means of an insertion aid from which the implant is then to be disconnected. Implants under the scope of the invention are also such objects that are designed for optional detachment only and may either remain in the body or be removed from it depending on relevant treatment necessities. Examples in this respect are detachable stent-retrieval systems designed for the removal or displacement of thrombi.

Advantageously, the detachment element consists of one or several wires. The wires effectively lend themselves to transmit thrust or pull forces, which enables the attending physician not only to easily advance but also retract the implant. Ease of positioning is an important factor for the attending physician to be able to accurately move the implant to the desired placement site.

The single or multiple wires may have a round, square, oval or tubular cross section. Optional wire combinations may be employed in this case, for example combinations consisting of round and square wires. The wires are usually manufactured by drawing and thus reducing the raw material to the desired final cross section. The wire structure and thus the detachment characteristics of the detachment element can thus be influenced by the drawing process. By varying cross section and form of the wires these can be optimally adapted to suit the relevant application needs.

To simplify the detachment process further the detachment elements may be subjected to a surface treatment. For example, roughening the surface will result in accelerating the dissolution because this will cause the surface of the detachment element to be enlarged. There are other known possibilities to bring about a quicker dissolution of the detachment element by adopting an additional treatment method as has been described for instance in WO 03/017852 A1 mentioned hereinbefore to which reference is made in this respect. The detachment element may, for example, be subjected to a heat treatment bringing about a precipitation process which causes the metal structure to be modified such that it very quickly disintegrates in an electrolyte when an electric voltage is applied. Such a heat treatment can be performed with the help of a laser, in a furnace or by means of an induction coil, Expediently, the cooling down process is to be effected relatively quickly by quenching. In this manner structural conditions are created which promote electrolytic dissolution.

During heating and cooling cobalt passes through a reversible allotropic phase transformation. At high temperature the cubic face-centered phase ($\alpha$-cobalt) is stable with its transformation to yield hexagonal $\epsilon$-cobalt occurring during the cooling down process at approx. 420° C. While it is quite difficult to transform $\epsilon$-cobalt the metastable $\alpha$-phase is more ductile. The transformation temperature can be varied by appropriately selecting different alloying components.

Basically, additions of chrome, molybdenum or tungsten result in the hexagonal phase being stabilized and the stacking fault energy being reduced while the elements iron, nickel and manganese advance the cubic phase and increase the stacking fault energy. After solution annealing the alloy normally consists mainly of $\alpha$-cobalt, while a subsequent cold forming step (e.g. wire drawing) and/or precipitation processes cause the $\epsilon$-cobalt content to be increased. By precipitation hardening intermetallic phases can be eliminated from the alloy which leads to a higher susceptibility of the alloy to corrosion. Finally, the alloy should primarily be metastable as $\alpha$-cobalt but also contain a certain amount of $\epsilon$-cobalt.

Other additional treatment methods such as pre-corrosion are also conceivable, for example by means of pre-etching. Moreover, detachment may also be accelerated passively by the designwise formation of local corrosion elements. Such corrosion elements form when different noble metals are arranged next to each other, i.e. the detachment element is made of a metal less noble than the implant and/or the insertion aid.

The dissolution of the detachment element is brought about by applying an electrical voltage. The electric power may be alternate current or direct current, with a minor current intensity (<3 mA) being sufficient. The detachment element in this case functions as anode the metal of it being oxidized and dissolved.

To make it possible to actively influence the dissolution more effectively it may be expedient to design the detachment element in such a manner that formation of the above described local corrosion elements is avoided. This may be brought about e.g. by insulating the detachment element against adjacent areas of the device, for instance by means of insulating adhesive connections to be arranged between detachment element and implant.

The electrolytic severance is achieved by making use of a power source to apply an electric voltage to the detachment element. In this case the detachment element acts as anode whereas the cathode is placed on the surface of the body. It is to be understood that the detachment element must be connected in an electrically conductive manner with the power source, in particular via the insertion aid. For this purpose the insertion aid itself must also be of electrically conductive design. Due to the fact that the corrosion-inducing current is influenced by the surface of the cathode, said cathode surface should be significantly greater than the surface of the anode. To a certain extent the speed at which the detachment element is dissolved can be controlled by appropriately sizing the cathode surface in relation to the anode surface. Accordingly, the invention also relates to a device comprising a power source and, where applicable or appropriate, an electrode to be placed onto the body surface.

Further steps may be carried out alternatively or additionally to support or aid the dissolution or severance of the detachment element. Mention shall be made in this context of the use of light waves, sound (ultrasound) or magnetic force.

It is, moreover, considered expedient to arrange for a securing means to be run through the implant. Securing means of this nature offer advantages by making the retraction of the implant into the catheter significantly safer which is necessary in case it has been wrongly positioned. Retracting, for example, an occlusion helix without securing means involves a risk in that portions of the helix are pulled apart and elongated due to the tensile or torsional stresses applied and in this way be plastically deformed irreversibly. In extreme cases the helix may separate or break giving rise to life-threatening embolism. Known from prior art are securing means made of flexible polymer threads or materials having shape-memory properties.

Publications also proposed the provision of devices comprising several detachment elements so that in case of need implants of variable length could be placed in position at the target location. In this manner it is possible, for instance, to place occlusion helixes of absolutely correct length in the aneurysm. Reference in this context is made to WO 01/32085 A1.

The application of such implants having a plurality of electrolytically corrodible locations is based on findings according to which the specific severance location of the implant situated nearest to the distal end of the catheter is dissolved by electrolysis when a current is applied to such a device. This is due to the fact in that on the one hand the detachment locations in the catheter are isolated from the ionic medium through the catheter and thus not affected by electrolysis and, on the other hand, the current density decreases from proximal to distal owing to the distally increasing resistance. As a result of this, the electrolytically corrodible point which, viewed in distal direction, is closest to the distal end of the catheter is subjected to the most intensive electrolytic process and is thus preferentially dissolved.

The implants are in particular made of platinum or platinum alloys which have proven their worth. Such materials are also beneficial in that they have radiopaque properties and thus enable the placement of the implant to be easily monitored visually. The cobalt-chrome alloys employed for the detachment element are as a rule MR compatible and therefore enable visualization to be performed.

The device according to the invention may also be directly combined with a micro-catheter by means of which the implant is brought to its placement site. The catheter and the implant used in this case shall be matched with respect to their size. If necessary, the catheter also may exert constraint on the implant resulting in the implant to only assume a previously impressed secondary structure when it has been liberated and released from such constraint. Additionally, the catheter is moreover provided with radiopaque markers enabling a positioning in the target area with the help of known imaging methods.

The detachment element typically has a length ranging between 0.05 and 0.5 mm, in particular approx. 0.2 mm, and a diameter of between 0.04 and 0.5 mm, in particular of approx. 0.1 mm.

Further elucidation of the invention is provided through the enclosed FIG. 1 which illustrates the schematic design of the inventive device.

The device consists of an implant 1, an insertion aid 2 and a detachment element 3, wherein said insertion aid 2 is arranged at the proximal end of the device and the implant 1 at its distal end as viewed in the direction into which the device is advanced. The implant 1 is transferred to its placement site by moving the insertion aid 2 forward in a catheter not illustrated in the figure.

The invention claimed is:

1. Device comprising an endovascular implant (1) for the introduction into blood vessels or body cavities of the human or animal body and an insertion aid (2), wherein the implant (1) and the insertion aid (2) are connected to each other via a detachment element (3) made of a metal less noble than the implant or the insertion aid metal and designed to be electrolytically corrodible and severed so that after the implant (1) has been inserted into the body and a voltage has been applied, severance by dissolution of the detachment element (3) takes place causing the implant (1) to be separated from the insertion aid (2), wherein the detachment element (3) is made of a cobalt-chrome alloy containing at least 20% w/w cobalt and 10 to 40% w/w chrome.

2. Device according to claim 1, wherein the cobalt-chrome alloy contains up to 70% w/w of cobalt.

3. Device according to claim 2, wherein the cobalt-chrome alloy contains between 30 and 60% w/w of cobalt.

4. Device according to claim 1, wherein the cobalt-chrome alloy contains between 15 and 30% w/w of chrome.

5. Device according to claim 1 wherein the cobalt-chrome alloy contains between 4 and 12% w/w of molybdenum.

6. Device according to claim 1, wherein the cobalt-chrome alloy contains between 8 and 40% w/w of nickel.

7. Device according to claim 1, wherein the cobalt-chrome alloy contains between 5 and 20% w/w of tungsten.

8. Device according to any one of claim 1, wherein the cobalt-chrome alloy contains up to 30% w/w of manganese.

9. Device according to claim 1, wherein the cobalt-chrome alloy contains up to 30% w/w of iron.

10. Device according to claim 1, wherein the insertion aid is a guide wire (2).

11. Device according to claim 1, wherein the implant (1) is an occlusion helix, a stent, a detachable stent retrieval system or a stent-like system devised so as to influence the flow of blood.

12. Device according to claim 1, wherein the detachment element (3) consists of one or several wires.

13. Device according to claim 12, wherein the one or several wires have a round, square, oval and/or tubular cross section.

14. Device according to claim 1, wherein the detachment element (3) has a rough surface.

15. Device according to claim 1, wherein the detachment element (3) is pre-corroded.

16. Device according to claim 1, wherein the detachment element (3) or the alloy of which the detachment element (3) is to be manufactured is subjected to a heat treatment.

17. Device according to claim 1, wherein said device is provided in combination with a micro-catheter.

18. Device comprising an endovascular implant (1) for the introduction into blood vessels or body cavities of the human or animal body and an insertion aid (2), wherein the implant (1) and the insertion aid (2) are connected to each other via a detachment element (3) designed to be electrolytically corrodible and severed so that after the implant (1) has been inserted into the body and a voltage has been applied, severance by dissolution of the detachment element (3) takes place causing the implant (1) to be separated from the insertion aid (2), wherein the detachment element (3) is made of a cobalt-chrome alloy containing at least 20% w/w cobalt and 10 to 40% w/w chrome and does not form a local corrosion element.

19. Device comprising an endovascular implant (1) for the introduction into blood vessels or body cavities of the human or animal body and an insertion aid (2), wherein the implant (1) and the insertion aid (2) are connected to each other via a detachment element (3) designed to be electrolytically corrodible and severed so that after the implant (1) has been inserted into the body and a voltage has been applied, severance by dissolution of the detachment element (3) takes place causing the implant (1) to be separated from the insertion aid (2), wherein the detachment element (3) is made of a cobalt-chrome alloy containing at least 20% w/w cobalt and 10 to 40% w/w chrome and is insulated against the implant.

* * * * *